(12) United States Patent
Barthe et al.

(10) Patent No.: US 8,460,193 B2
(45) Date of Patent: Jun. 11, 2013

(54) SYSTEM AND METHOD FOR ULTRA-HIGH FREQUENCY ULTRASOUND TREATMENT

(75) Inventors: Peter G. Barthe, Phoenix, AZ (US); Michael H Slayton, Tempe, AZ (US)

(73) Assignee: Guided Therapy Systems LLC, Mesa, AZ (US)

( * ) Notice: Subject to any disclaimer, the term of this patent is extended or adjusted under 35 U.S.C. 154(b) by 0 days.

(21) Appl. No.: 12/792,934

(22) Filed: Jun. 3, 2010

(65) Prior Publication Data

US 2010/0241035 A1   Sep. 23, 2010

Related U.S. Application Data

(63) Continuation of application No. 11/245,999, filed on Oct. 6, 2005, now Pat. No. 7,758,524.

(60) Provisional application No. 60/616,356, filed on Oct. 6, 2004.

(51) Int. Cl.
*A61B 8/00* (2006.01)

(52) U.S. Cl.
USPC .............. 600/437; 600/407; 600/439; 601/2; 601/3; 601/4; 604/22

(58) Field of Classification Search
USPC .............. 601/2–4; 600/407, 437, 439; 604/22
See application file for complete search history.

(56) References Cited

U.S. PATENT DOCUMENTS

| | | |
|---|---|---|
| 2,427,348 A | 9/1947 | Bond et al. |
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,213,344 A | 7/1980 | Rose |
| 4,276,491 A | 6/1981 | Daniel |
| 4,315,514 A | 2/1982 | Drewes et al. |

(Continued)

FOREIGN PATENT DOCUMENTS

| | | |
|---|---|---|
| DE | 4029175 | 3/1992 |
| DE | 10140064 | 3/2003 |

(Continued)

OTHER PUBLICATIONS

Chen, L. et al., ""Effect of Blood Perfusion on the ablation of liver perenchyma with high intensity focused ultrasound,"" Phys. Med. Biol; 38:1661-1673; 1993b.

(Continued)

*Primary Examiner* — Peter Luong
(74) *Attorney, Agent, or Firm* — Michael J. Lang

(57) ABSTRACT

A non-invasive ultra-high frequency ultrasound treatment method and system are provided. An exemplary method and system comprise a high-frequency ultrasound transducer system configured for providing ultrasound treatment to a patient such that the superficial and/or subcutaneous regions of the patient can be treated. An exemplary high-frequency ultrasound transducer system comprises a control system and a transducer configured to provide treatment to the superficial and/or subcutaneous regions of interest. The high-frequency ultrasound transducer may be configured to operate at higher frequencies and controlled power levels to provide treatment to the superficial and/or subcutaneous regions of interest. For example, higher frequencies within the range from approximately 20 MHz to 500 MHz or more may be utilized.

7 Claims, 3 Drawing Sheets

U.S. PATENT DOCUMENTS

| | | |
|---|---|---|
| 4,325,381 A | 4/1982 | Glenn |
| 4,343,301 A | 8/1982 | Indech |
| 4,372,296 A | 2/1983 | Fahim |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,441,486 A | 4/1984 | Pounds |
| 4,452,084 A | 6/1984 | Taenzer |
| 4,484,569 A | 11/1984 | Driller |
| 4,513,749 A | 4/1985 | Kino |
| 4,527,550 A | 7/1985 | Ruggera et al. |
| 4,528,979 A | 7/1985 | Marchenko |
| 4,567,895 A | 2/1986 | Putzke |
| 4,586,512 A | 5/1986 | Do-huu |
| 4,601,296 A | 7/1986 | Yerushalmi |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,697,588 A | 10/1987 | Reichenberger |
| 4,757,820 A | 7/1988 | Itoh |
| 4,807,633 A | 2/1989 | Fry |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,893,624 A | 1/1990 | Lele |
| 4,896,673 A | 1/1990 | Rose |
| 4,917,096 A | 4/1990 | Englehart |
| 4,973,096 A | 4/1990 | Jaworski |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 5,012,797 A | 5/1991 | Liang |
| 5,036,855 A | 8/1991 | Fry |
| 5,054,310 A | 10/1991 | Flynn |
| 5,054,470 A | 10/1991 | Fry |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,150,711 A | 9/1992 | Dory |
| 5,150,714 A | 9/1992 | Green |
| 5,156,144 A | 10/1992 | Iwasaki |
| 5,158,536 A | 10/1992 | Sekins |
| 5,163,421 A | 11/1992 | Bernstein |
| 5,191,880 A | 3/1993 | McLeod |
| 5,209,720 A | 5/1993 | Unger |
| 5,224,467 A | 7/1993 | Oku |
| 5,230,334 A | 7/1993 | Klopotek |
| 5,230,338 A | 7/1993 | Allen et al. |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,304,169 A | 4/1994 | Sand |
| 5,321,520 A | 6/1994 | Inga et al. |
| 5,360,268 A | 11/1994 | Hayashi |
| 5,370,121 A | 12/1994 | Reichenberger |
| 5,371,483 A | 12/1994 | Bhardwaj |
| 5,380,280 A | 1/1995 | Peterson |
| 5,391,140 A | 2/1995 | Schaetzle |
| 5,391,197 A | 2/1995 | Burdette et al. |
| 5,406,503 A | 4/1995 | Williams, Jr. et al. |
| 5,419,327 A | 5/1995 | Rohwedder |
| 5,435,311 A | 7/1995 | Umemura |
| 5,458,596 A | 10/1995 | Lax |
| 5,460,595 A | 10/1995 | Hall et al. |
| 5,471,988 A | 12/1995 | Fujio |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,638,819 A | 6/1997 | Manwaring et al. |
| 5,647,373 A | 7/1997 | Paltieli |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,665,053 A | 9/1997 | Jacobs |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,769,790 A | 6/1998 | Watkins |
| 5,795,297 A | 8/1998 | Daigle |
| 5,795,311 A | 8/1998 | Wess |
| 5,810,888 A | 9/1998 | Fenn |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,871,524 A | 2/1999 | Knowlton |
| 5,873,902 A | 2/1999 | Sanghvi |
| 5,879,303 A | 3/1999 | Averkiou et al. |
| 5,882,557 A | 3/1999 | Hayakawa |
| 5,891,034 A | 4/1999 | Bucholz |
| 5,904,659 A | 5/1999 | Duarte |
| 5,919,219 A | 7/1999 | Knowlton |

| Patent | Date | Inventor |
|---|---|---|
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,967,980 A | 10/1999 | Ferre et al. |
| 5,968,034 A | 10/1999 | Fullmer |
| 5,971,949 A | 10/1999 | Levin |
| 5,984,882 A | 11/1999 | Rosenschein |
| 5,997,471 A | 12/1999 | Gumb et al. |
| 5,997,497 A | 12/1999 | Nita et al. |
| 6,004,262 A | 12/1999 | Putz et al. |
| 6,007,499 A | 12/1999 | Martin et al. |
| 6,036,646 A | 3/2000 | Barthe |
| 6,039,048 A | 3/2000 | Silberg |
| 6,042,556 A | 3/2000 | Beach et al. |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,086,535 A | 7/2000 | Ishibashi |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein |
| 6,113,559 A | 9/2000 | Klopotek |
| 6,120,452 A | 9/2000 | Barthe |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,769 B1 | 12/2001 | Klopotek |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,253 B1 | 7/2002 | Koop |
| 6,413,254 B1 | 7/2002 | Hissong |
| 6,419,648 B1 | 7/2002 | Vitek |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,491,657 B2 | 12/2002 | Rowe |
| 6,500,121 B1 | 12/2002 | Slayton |
| 6,500,141 B1 | 12/2002 | Irion |
| 6,508,774 B1 | 1/2003 | Acker |
| 6,511,428 B1 | 1/2003 | Azuma |
| 6,514,244 B2 | 2/2003 | Pope |
| 6,524,250 B1 | 2/2003 | Weber |
| 6,540,679 B2 | 4/2003 | Slayton |
| 6,540,685 B1 | 4/2003 | Rhoads et al. |
| 6,554,771 B1 | 4/2003 | Buil et al. |
| 6,569,099 B1 | 5/2003 | Babaev |
| 6,595,934 B1 | 7/2003 | Hissong |
| 6,599,256 B1 | 7/2003 | Acker |
| 6,607,498 B2 | 8/2003 | Eshel |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B2 | 12/2003 | Shimizu |
| 6,666,835 B2 | 12/2003 | Martin |
| 6,669,638 B1 | 12/2003 | Miller et al. |
| 6,685,640 B1 | 2/2004 | Fry |
| 6,692,450 B1 | 2/2004 | Coleman |
| 6,699,237 B2 | 3/2004 | Weber |
| 6,719,449 B1 | 4/2004 | Laughran, Jr. et al. |
| 6,719,694 B2 | 4/2004 | Weng |
| 6,825,176 B2 | 4/2004 | Mourad |
| 6,749,624 B2 | 6/2004 | Knowlton |
| 6,775,404 B1 | 8/2004 | Pagoulatos et al. |
| 6,824,516 B2 | 11/2004 | Batten et al. |
| 6,835,940 B2 | 12/2004 | Morikawa et al. |
| 6,875,176 B2 | 4/2005 | Mourad et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,936,044 B2 | 8/2005 | McDaniel |
| 6,936,046 B2 * | 8/2005 | Hissong et al. .................. 606/27 |
| 6,948,843 B2 | 9/2005 | Laughran et al. |
| 6,953,941 B2 | 10/2005 | Nakano et al. |
| 6,958,043 B2 | 10/2005 | Hissong |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 * | 7/2006 | Vaezy et al. .................. 600/459 |
| 7,074,218 B2 | 7/2006 | Washington et al. |
| 7,094,252 B2 | 8/2006 | Koop |
| 7,115,123 B2 | 10/2006 | Knowlton |

| | | |
|---|---|---|
| 7,142,905 B2 | 11/2006 | Slayton |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,297,117 B2 | 11/2007 | Trucco et al. |
| 7,347,855 B2 | 3/2008 | Eshel |
| RE40,403 E | 6/2008 | Cho et al. |
| 7,393,325 B2 | 7/2008 | Barthe |
| 7,491,171 B2 | 2/2009 | Barthe et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,758,524 B2 | 7/2010 | Barthe |
| 7,824,348 B2 | 11/2010 | Barthe et al. |
| 7,955,281 B2 | 6/2011 | Pedersen et al. |
| 8,057,389 B2 | 11/2011 | Barthe et al. |
| 8,128,618 B2 | 3/2012 | Gliklich et al. |
| 8,282,554 B2 | 10/2012 | Makin et al. |
| 2001/0009997 A1 | 7/2001 | Pope |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0082528 A1 | 6/2002 | Friedman et al. |
| 2002/0082589 A1 | 6/2002 | Friedman et al. |
| 2002/0095143 A1 | 7/2002 | Key |
| 2002/0128648 A1 | 9/2002 | Weber |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193831 A1 | 12/2002 | Smith |
| 2003/0014039 A1 | 1/2003 | Barzell et al. |
| 2003/0018255 A1 | 1/2003 | Martin |
| 2003/0028113 A1 | 2/2003 | Gilbert et al. |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra |
| 2003/0060736 A1* | 3/2003 | Martin et al. ............ 601/2 |
| 2003/0065313 A1 | 4/2003 | Koop |
| 2003/0074023 A1 | 4/2003 | Kaplan |
| 2003/0083536 A1 | 5/2003 | Eshel |
| 2003/0097071 A1 | 5/2003 | Halmann et al. |
| 2003/0125629 A1 | 7/2003 | Ustuner |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0059266 A1 | 3/2004 | Fry |
| 2004/0073079 A1 | 4/2004 | Altshuler et al. |
| 2004/0073113 A1 | 4/2004 | Salgo |
| 2004/0073116 A1 | 4/2004 | Smith |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste et al. |
| 2004/0267252 A1 | 12/2004 | Washington |
| 2005/0033201 A1 | 2/2005 | Takahashi |
| 2005/0055073 A1 | 3/2005 | Weber |
| 2005/0070961 A1 | 3/2005 | Maki et al. |
| 2005/0074407 A1 | 4/2005 | Smith |
| 2005/0080469 A1 | 4/2005 | Larson |
| 2005/0113689 A1 | 5/2005 | Gritzky |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0228281 A1 | 10/2005 | Nefos |
| 2005/0240170 A1 | 10/2005 | Zhang et al. |
| 2005/0256406 A1 | 11/2005 | Barthe |
| 2005/0261584 A1 | 11/2005 | Eshel |
| 2005/0267454 A1 | 12/2005 | Hissong |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich |
| 2007/0035201 A1 | 2/2007 | Desilets |
| 2007/0055154 A1 | 3/2007 | Torbati |
| 2007/0055156 A1 | 3/2007 | Desilets |
| 2007/0087060 A1 | 4/2007 | Dietrich |
| 2007/0088346 A1 | 4/2007 | Mirizzi et al. |
| 2007/0167709 A1 | 7/2007 | Slayton |
| 2007/0208253 A1 | 9/2007 | Slayton |

| | | | | | | |
|---|---|---|---|---|---|---|
| 2007/0239075 | A1 | 10/2007 | Rosenberg et al. | KR | 1020060113930 | 11/2006 |
| 2008/0027328 | A1 | 1/2008 | Klopotek et al. | KR | 1020070065332 | 6/2007 |
| 2008/0039724 | A1 | 2/2008 | Seip et al. | KR | 1020070070161 | 7/2007 |
| 2008/0071255 | A1 | 3/2008 | Barthe | KR | 1020070098856 | 10/2007 |
| 2008/0086054 | A1 | 4/2008 | Slayton | KR | 1020070104878 | 10/2007 |
| 2008/0097253 | A1 | 4/2008 | Pedersen | KR | 1020070114105 | 11/2007 |
| 2008/0167556 | A1 | 7/2008 | Thompson et al. | WO | 9625888 | 8/1996 |
| 2008/0200813 | A1 | 8/2008 | Quistgaard | WO | 9735518 | 10/1997 |
| 2008/0214966 | A1 | 9/2008 | Slayton | WO | 9832379 | 7/1998 |
| 2008/0221491 | A1 | 9/2008 | Slayton | WO | 9933520 | 7/1999 |
| 2008/0275342 | A1 | 11/2008 | Barthe | WO | 9949788 | 10/1999 |
| 2008/0281237 | A1 | 11/2008 | Slayton | WO | 0006032 | 2/2000 |
| 2008/0281255 | A1 | 11/2008 | Slayton | WO | 0015300 | 3/2000 |
| 2008/0294073 | A1 | 11/2008 | Barthe | WO | 0021612 | 4/2000 |
| 2008/0319356 | A1 | 12/2008 | Cain et al. | WO | 0053113 | 9/2000 |
| 2009/0069677 | A1 | 3/2009 | Chen et al. | WO | 0128623 | 4/2001 |
| 2009/0182231 | A1 | 7/2009 | Barthe et al. | WO | 0182777 | 11/2001 |
| 2009/0216159 | A1 | 8/2009 | Slayton et al. | WO | 0182778 | 11/2001 |
| 2009/0253988 | A1 | 10/2009 | Slayton et al. | WO | 0187161 | 11/2001 |
| 2009/0318909 | A1 | 12/2009 | Debenedictis et al. | WO | 0209813 | 2/2002 |
| 2010/0011236 | A1 | 1/2010 | Barthe et al. | WO | 0224050 | 3/2002 |
| 2010/0022922 | A1 | 1/2010 | Barthe et al. | WO | 02092168 | 11/2002 |
| 2010/0160782 | A1 | 6/2010 | Slayton et al. | WO | 03065347 | 8/2003 |
| 2010/0241035 | A1 | 9/2010 | Barthe et al. | WO | 03070105 | 8/2003 |
| 2010/0280420 | A1 | 11/2010 | Barthe et al. | WO | 03077833 | 8/2003 |
| 2011/0112405 | A1 | 5/2011 | Barthe et al. | WO | 03086215 | 10/2003 |
| 2011/0178444 | A1 | 7/2011 | Slayton et al. | WO | 03096883 | 11/2003 |
| 2012/0016239 | A1 | 1/2012 | Barthe et al. | WO | 03099177 | 12/2003 |
| 2012/0029353 | A1 | 2/2012 | Slayton et al. | WO | 03101530 | 12/2003 |
| 2012/0035475 | A1 | 2/2012 | Barthe et al. | WO | 2004080147 | 9/2004 |
| 2012/0035476 | A1 | 2/2012 | Barthe et al. | WO | 2004110558 | 12/2004 |
| 2012/0046547 | A1 | 2/2012 | Barthe et al. | WO | 2005065408 | 7/2005 |
| 2012/0053458 | A1 | 3/2012 | Barthe et al. | WO | 2005090978 | 9/2005 |
| 2012/0111339 | A1 | 5/2012 | Barthe et al. | WO | 2006036870 | 4/2006 |
| 2012/0143056 | A1 | 6/2012 | Slayton et al. | WO | 2006042168 | 4/2006 |
| 2012/0165668 | A1 | 6/2012 | Slayton et al. | WO | 2006042201 | 4/2006 |
| 2012/0165848 | A1 | 6/2012 | Slayton et al. | WO | 2006065671 | 6/2006 |
| 2012/0197120 | A1 | 8/2012 | Makin et al. | WO | 2006082573 | 8/2006 |
| 2012/0197121 | A1 | 8/2012 | Slayton et al. | WO | 2009013729 | 1/2009 |
| 2012/0215105 | A1 | 8/2012 | Slayton et al. | | | |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 | 12/1989 |
| EP | 1479412 | 11/1991 |
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2009518126 | 5/2009 |
| JP | 2010517695 | 5/2010 |
| KR | 1020010024871 | 3/2001 |

OTHER PUBLICATIONS

Damianou et al., Application of the Thermal Dose Concept for Predicting the Necrosed Tissue Volume During Ultrasound Surgery, 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

Simon et al., "Applications of Lipid-Coated Microbubble Ultrasonic Contrast to Tumor Therapy," Ultrasound in Med. & Biol. vol. 19, No. 2, pp. 123-125 (1993).

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US-Therapy", 1994 Ultrasonics Symposium, pp. 1879-1882.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al., "Elastographic Characterization of HIFU-Induced Lesions in Canine Livers," 1999, Ultrasound in Med & Bio, vol. 25, No. 7, pp. 1099-1113.

Sanghvi, N.T., et al., "Transrectal Ablation of Prostrate Tissue Using Focused Ultrasound," 1993 Ultrasonics Symposium, IEEE, pp. 1207-1210.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Sassen, Sander, "ATI's R520 architecture, the new king of the hill?" http://www.hardwareanalysis.com/content/article/1813, Sep. 16, 2005, 2 pages.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

Arthur et al., "Non-invasive estimation of hyperthermia temperatures with ultrasound," Int. J. Hyperthermia, Sep. 2005, 21(6), pp. 589-600.

International Search Report and Written Opinion dated Mar. 28, 2012 in Application No. PCT/US2011/001362.

* cited by examiner

SYSTEM AND METHOD FOR ULTRA-HIGH FREQUENCY ULTRASOUND TREATMENT

CROSS-REFERENCE TO RELATED APPLICATIONS

This application is a continuation of U.S. application Ser. No. 11/245,999 entitled "SYSTEM AND METHOD FOR ULTRA-HIGH FREQUENCY ULTRASOUND TREATMENT" which was filed on Oct. 6, 2005, now U.S. Pat. No. 7,758,524, which in turn claims priority to and benefit of U.S. Provisional Application No. 60/616,356, entitled "System and Method for Ultra-High Frequency", and filed on Oct. 6, 2004, all of which are incorporated herein by reference.

FIELD OF INVENTION

This invention generally relates to an ultrasound system, and more particularly, to a method and system for ultra-high frequency ultrasound treatment.

BACKGROUND OF THE INVENTION

Many conventional applications of therapeutic ultrasound have employed low frequency transducers. These transducers have operational frequencies that typically range from 500 kHz to 1.5 MHz. Such low frequency transducers are often preferred because they allow for acoustical energy to be focused very deep into the body, without harming the overlying tissue structures.

A conventional application of non-invasive therapeutic ultrasound using a low frequency transducer is depicted in FIG. 1. A conventional low-frequency therapeutic application 100 utilizes low frequency energy 102 to treat a deep treatment region 104, such as a deep-seated lesion. Deep treatment region 104 is located at a depth well below a superficial region of a patient. Use of the low-frequency transducer generates an isonified tissue region 106 that can range from 2 cm to 10 cm below the skin surface. Unfortunately, currently available low frequency transducers cannot be used to treat the superficial regions, thus limiting the use of low-frequency application 100. For example, most cosmetic surgeries, as well as treatment of melanomas and skin disorders, require treatment to superficial regions, thus eliminating the use of lower frequency transducers.

Another undesirable side effect of low-frequency therapy is that the acoustic energy must pass through intervening tissue layers before reaching the desired deep treatment area. The intervening layers tend to defocus the rays and absorb some of the acoustic energy. This causes the focal spot size to widen, making it difficult to control the location of the focal spot, and making dosimetry also difficult to optimize.

SUMMARY OF THE INVENTION

In accordance with various aspects of the present invention, a non-invasive ultra-high frequency ultrasound treatment method and system are provided. An exemplary method and system comprise an ultra-high frequency ultrasound transducer system configured for providing ultrasound treatment to a patient such that the superficial regions of the patient can be treated extracorporeally and internal tissues can be treated superficially in a minimally invasive fashion.

An exemplary ultra-high frequency ultrasound transducer system comprises a control system and a transducer configured to provide treatment to the superficial and/or internal superficial regions of interest. The ultra-high frequency ultrasound transducer may be configured to operate at higher frequencies and controlled power levels to provide safe, controlled treatment to superficial, and/or internal superficial tissue, e.g. an organ or tissue surface regions of interest. For example, higher frequencies within the range from approximately 20 MHz to 500 MHz or more may be utilized. In addition, by operating at optimum efficiency, the acoustic intensity can be suitably configured at high levels with the use of controlled, moderate power output levels. In accordance with an exemplary embodiment of the present invention, the ultra-high frequency ultrasound transducer can comprise a transduction element having a piezoelectrically active layer, matching layers and/or other materials for generating radiation or acoustical energy. The transduction element can comprise single or multiple elements.

In accordance with an exemplary embodiment of the present invention, the transduction element may be configured with an application device to facilitate coupling of the acoustical energy to the superficial and/or internal superficial regions of interest. The application device may be configured in various manners for coupling to the patient to provide treatment to the superficial and/or internal superficial regions of interest. In accordance with another exemplary embodiment, the transduction element may be configured on a minimally-invasive application device, such as a needle or other medical instrument, to permit the transduction element to come into substantially direct contact with various facia, e.g., the SMAS tissue layers, to facilitate treatment. Thus, instead of being placed on the outer surface of the skin, the application device may be inserted into the patient to come into more proximate acoustical contact with the targeted region for treatment.

In accordance with an exemplary embodiment of the present invention, an exemplary control system comprises a drive circuit and a feedback network configured to control the operation of the ultra-high frequency ultrasound transducer. The drive circuit is configured to control power to the transduction element and can comprise various configurations, with and without voltage oscillation. In accordance with an exemplary embodiment, the drive circuit is configured to drive the frequency of the transduction element at the resonant frequency to facilitate maximum efficiency and/or maximum acoustic output. The feedback element is configured to use electrical signals from the driver circuit and/or the transduction element to facilitate control of the frequency of operation to provide optimum electro-acoustic conversion of energy. In addition, the control system can be suitably coupled to the transduction element in various manners.

In accordance with another aspect of the present invention, an ultra-high frequency ultrasound transducer system configured for providing ultrasound treatment to various depth regions within the superficial and/or internal superficial regions of the patient through control of the frequency of the transduction element and/or the cooling of the exemplary applicator device is provided.

BRIEF DESCRIPTION OF THE DRAWINGS

The subject matter of the invention is particularly pointed out and distinctly claimed in the concluding portion of the specification. The invention, however, both as to organization and method of operation, may best be understood by reference to the following description taken in conjunction with the claims and the accompanying drawing figures, in which like parts may be referred to by like numerals:

DETAILED DESCRIPTION

The present invention may be described herein in terms of various components and processing steps. It should be appreciated that such components and steps may be realized by any number of hardware devices and components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical or treatment contexts and that the exemplary embodiments relating to ultra-high frequency ultrasound treatment as described herein are merely a few of the exemplary applications for the invention. For example, the principles, features and methods discussed may be applied to any medical or other tissue or treatment application.

In accordance with various aspects of the present invention, a non-invasive ultra-high frequency ultrasound treatment method and system are provided. An exemplary method and system comprise an ultra-high frequency ultrasound transducer system configured for providing ultrasound treatment to a patient such that superficial and/or internal superficial regions of a patient can be treated.

Figure 1:
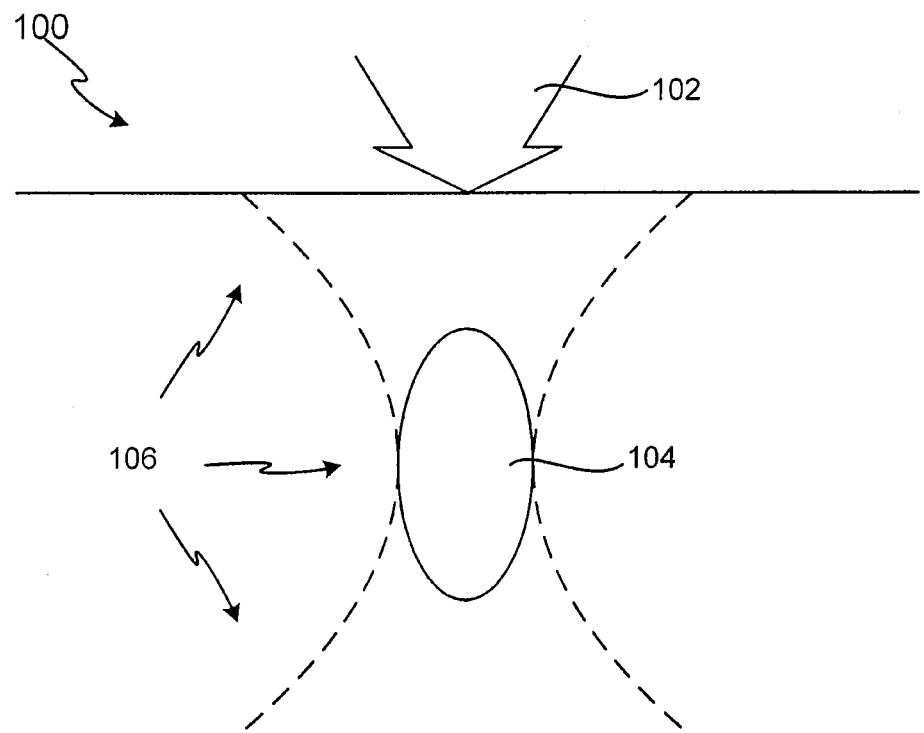
FIG. 1 illustrates a diagram of treatment application using a prior art low-frequency ultrasound treatment system.
Figure 2:
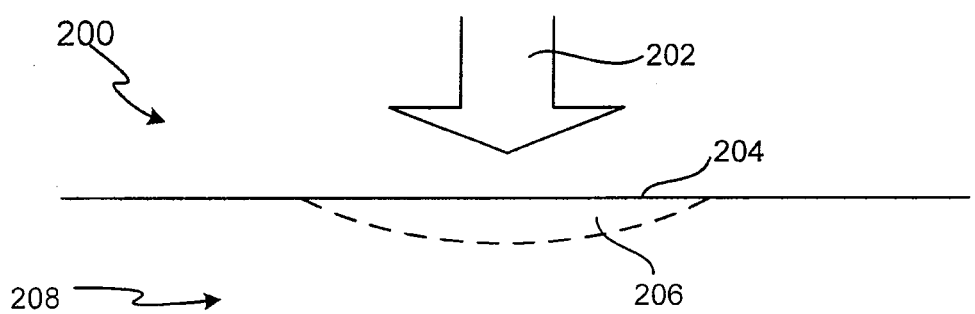
FIG. 2 illustrates a diagram of an ultra-high frequency ultrasound treatment application in accordance with an exemplary embodiment of the present invention.

With reference to FIG. 2, an exemplary ultra-high frequency ultrasound application 200 can comprise the applying of ultra-high frequency acoustical energy 202 to a superficial region 204 and/or internal superficial region 206 of a patient. Superficial region 204 comprises the skin layer of a patient, e.g., the outermost epidermis layer that can comprise between approximately 0.1 μm to 100 μm and the inner dermis layer between approximately 0.1 mm and 3 mm or more. The internal superficial region comprises the superficial layers of internal organs or tissue, for example between approximately 0 mm to 3 mm or more. Ultra-high frequency acoustical energy 202 is configured for operating at higher frequencies and suitable power levels such that the frequency dependent acoustic absorption provides treatment only at the superficial region 204 or internal superficial region.

For example, higher frequencies within the range from approximately 20 MHz to 500 MHz or more may be utilized to cause absorption within the regions of interest, such as within the epidermis layers and/or just below the dermis skin layers of the patient. Moreover, acoustic power levels may be configured to optimize the frequency dependent acoustic absorption at the ultra-high frequency levels to facilitate treatment to the regions of interest. By operating at optimum efficiency, the acoustic intensity can be suitably configured at high levels with the use of controlled, moderate power output levels. For example, for a steady-state ultrasound intensity of approximately 500 W/cm$^2$ at the outermost epidermis layer, the acoustical intensity can be configured to drop one to two orders of magnitude using the ultra-high frequencies, thus becoming highly absorbed as the energy penetrates the skin layers, e.g., at 300 MHz, the acoustical intensity drops to approximately 15 W/cm$^2$ at a depth of approximately 100 μm. As a result, the acoustic intensity is configured to be relatively large at the region of interest between superficial region 204 and treatment region 206, and then rapidly drop off to lower levels proximate to region 208. Accordingly, ultra-high frequency acoustical energy 202 can be used to suitably ablate superficial region 204, as well as internal superficial tissue and/or treat treatment region 206 while leaving region 208 unaffected.

Figure 3:
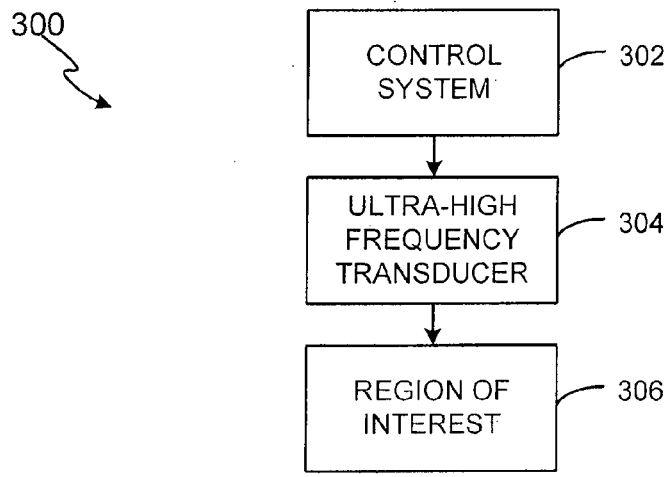
FIG. 3 illustrates a block diagram of an ultra-high frequency ultrasound treatment system in accordance with an exemplary embodiment of the present invention.

An exemplary high-frequency ultrasound transducer system can provide ultra-high frequency acoustical energy 202 in various configurations. For example, in accordance with an exemplary embodiment, with reference to FIG. 3, exemplary ultra-high frequency ultrasound system 300 comprises a control system 302 and a transducer 304 configured to provide treatment to a region of interest 306 within the superficial and/or internal superficial regions of a patient. In providing treatment, ultra-high frequency ultrasound system 300 may provide therapy, imaging and/or temperature monitoring to region of interest 306.

Control system 302 is configured for control and operation of transducer 304 to provide treatment. Control system 302 may comprise a processor, a display, and/or one or more input devices. In accordance with an exemplary embodiment, as discussed in more detail below, control system 302 can also comprise an electronic drive and control unit including a drive circuit, power supply and other electronic control devices that can be configured to drive the frequency of transducer 304 in a controlled manner for maximum efficiency. The processor may comprise a personal computer, a Unix system, or any other conventional processing unit. The display may comprise a monitor, LCD screen, or any other device configured to display an image. An input/output device may comprise a keyboard, a mouse, a touch-screen, or any other device for transmitting or receiving information to and from a control system. An "on/off" pushbutton or other control inputs may also be configured within control system 302. The information from the input device and images displayed may be received or transmitted in any format, such as manually, by analog device, by digital device, and/or by any other mechanisms.

The processor, display, electronic drive and control devices and/or input devices may be coupled together in any manner. By coupling, the devices comprising control system 304 may be directly connected to each other or may be connected through one or more other devices or components that allow a signal to travel to/from one component to another. The various coupling components for the devices comprising control system 304 can include but are not limited to the interne, a wireless network, a conventional wire cable, an optical cable or connection through air, water, or any other medium that conducts signals, and any other coupling device or medium.

Transducer 304 is configured to operate at ultra-high frequencies. For example, frequencies within the range from approximately 20 MHz to 400 MHz or more may be selected to cause acoustic absorption within region of interest 306, i.e., within the outer epidermis layers, and/or just below the skin layers of the patient through the subcutaneous fat region. In accordance with an exemplary embodiment, transducer 304 can also be configured to operate at suitable power levels through control system 302 to provide a desired level of frequency dependent acoustic absorption. In accordance with an exemplary embodiment of the present invention, transducer 304 can comprise a transduction element having a piezoelectrically active layer, matching layers and/or other materials for generating radiation or acoustical energy that can be coupled to region of interest 306 in various manners.

Figure 4A:
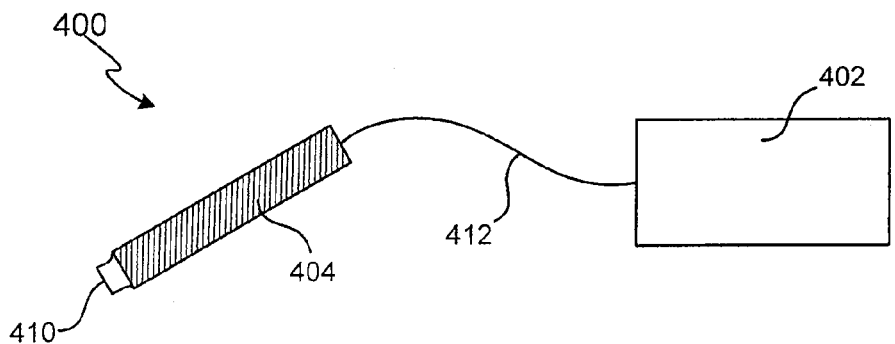
FIGS. 4A-4C illustrates a diagram of an ultra-high frequency ultrasound transducer system in accordance with an exemplary embodiment of the present invention.
Figure 4B:
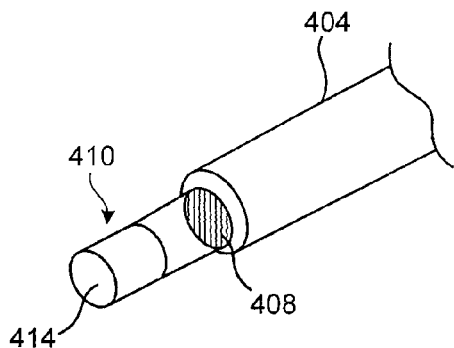
Figure 4C:
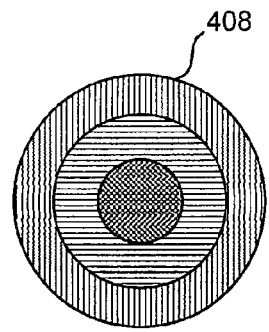

For example, with reference to FIGS. 4A-4C, in accordance with an exemplary embodiment of the present invention, an exemplary ultra-high frequency ultrasound system 400 comprises a control system 402 and a transducer 404. Control system 402 can comprise various circuit configurations for control of transducer 404, e.g., to provide drive signals to transducer 404. Control system 402 can also be coupled to transducer 404 in various manners, such as through a direct electrical connection through a cable 412, and/or through other coupling mechanisms, including capacitive coupling, thermo-acoustic coupling, and/or broadband, narrowband or high-pass acoustic filtering. Control system 402 can also be coupled to transducer 404 by inducing RF fields to transducer 404. For example, a periodic electric field can be polarized along the fully excited length of a transduction element within transducer 404, such as along the x-axis of a X-cut rod of crystalline quartz or other crystal or piezoelectric element or polarized ferroelectrics material.

In accordance with an exemplary embodiment, transducer 404 comprises a housing 406, a transduction element 408 and an application device 410. Housing 406 is suitably configured to enclose or encapsulate components of transducer 404. Housing 406 can comprise any conventional housing or enclosure suitably for containing transducer elements and components, and can be shaped and sized in various manners. For example, in accordance with an exemplary embodiment, housing 406 can be configured in the shape of a pen or stylus. However, housing 406 can be configured in any manner to allow for maneuvering and positioning of application device 410 along the skin surface of a patient.

Transduction element 408 can comprise a piezoelectrically active material, or any piezoelectric or polarized ferroelectric material, crystal, ceramic, plastic, and/or like composite materials. For example, transduction element 408 can comprise lead zirconante titanate (PZT), or any other piezoelectrically active material. Transduction element 408 can also comprise piezoelectric crystals, such as lithium niobate ($LiNbO_3$), lead titanate, barium titanate, quartz ($SiO_2$) and/or lead metaniobate, any polarized ferroelectric material, or any other crystals that possess low to very low dielectric and mechanical losses. Such elements and crystals can be suitably cut or shaped in various manners, such as Y-cut and X-cut configurations, e.g., an approximate 36-degree Y-cut lithium niobate crystal and an X-cut quartz crystal can exhibit excellent characteristics.

In addition to or instead of a piezoelectrically active material or crystals, transducer 404 may comprise any other materials configured for generating radiation and/or acoustical energy. Transducer 404 may also comprise one or more matching layers configured along with transduction element 408, e.g., coupled to the piezoelectrically active material, to optimize the acoustic output. For example, using matching layers designed for the fundamental resonant frequency of transduction element 408 can also cause matching of transduction element 408 at odd harmonic resonant frequencies as well. Any such matching layers can comprise thin films at higher frequencies, as opposed to thicker films used with low-frequency transducers that can vastly require an increase in acoustic power requirements.

The thickness of transduction element 408 of transducer 404 may be selected to provide a nominal or center operating frequency of a moderately high range, such as from approximately 10 MHz to 30 MHz or more, to facilitate greater resolution. For example, an approximately 4 mm diameter crystal, such as lithium niobate, having a 25 MHz nominal frequency can provide excellent efficiency, e.g., low dielectric losses, when operating at ultra-high frequencies, including within the range from approximately 20 MHz to 400 MHz or more. In addition, various crystalline materials can be suitably lapped in thickness to a high precision such that overtones, e.g., approximately odd harmonics, can be driven with high efficiency. Selecting the thickness of transduction element 408 and the resulting nominal frequency for operation can be based on the degree and balance of energy penetration and resolution that is desired for a treatment application.

Transduction element 408 can comprise a single transduction element for generating acoustical energy. Transduction element 408 can also comprise multiple elements, such as that illustrated in FIG. 4C. For example, transduction element 408 can be suitably diced in a plurality of sections that can be suitably configured to focus on the treatment region at a certain depth and/or spot size within the region of interest. Transduction element 408 can be configured as multiple elements in various arrangements, such as that set forth in U.S. application Ser. No. 11/163,148, filed Oct. 6, 2005, entitled "Method and System for Controlled Thermal Injury," published as US 2006-0116671 on Jun. 1, 2006, and hereby incorporated by reference. In addition, a multiple element configuration for transduction element 408 can also be configured with electronic focusing to provide spot-size control. Electronic focusing can be implemented in various manners, such as that set forth in U.S. application Ser. No. 10/944,500, filed Sep. 16, 2004, entitled "System and Method for Variable Depth Ultrasound," published as US 2006-0058664 on Mar. 16, 2006, and hereby incorporated by reference.

Application device 410 is configured to facilitate coupling of the acoustical energy to a region of interest, such as to the superficial and/or internal superficial regions. In accordance with an exemplary embodiment, application device 410 can comprise a standoff, a waveguide, or any other isolation/protection layer configured to enable transducer 404 to provide acoustical energy to the patient. Application device 410 can also comprise various sizes, shapes and configurations. For example, application device 410 can comprise a transparent, solid standoff such that a physician can precisely contact any small lesions in the epidermis region of the patient, and allow transducer 404 and application device 410 to be suitably sterilized for further use. In addition, application device 410 can comprise a non-transparent disposable applicator tip, and/or an applicator tip that can be suitably replaced for different patients. Applicator device 410 can also be configured in various lengths, for example as a long waveguide of several millimeters, or as a shorter applicator tip of approximately 1 mm to a few hundred micrometers in length. Shorter lengths can allow for more efficient acoustic output as compared to longer lengths for a waveguide that can alter the frequency response of the transduction element 408/applicator device 410. In any event, the selection of length can be based upon the desired operating characteristics.

Applicator device 410 may be configured in various manners for coupling to the patient to provide treatment to the superficial and/or internal superficial regions of interest. For example, applicator device 410 can comprise materials and composites having very low acoustical losses, such as fused silica, or any other low loss materials. In addition, a tip 414 of applicator device 410 can comprise a substantially flat shape for coupling to the outer skin layer of a patient, a concave-like depression configured to focus acoustic energy to the region of interest, and/or an optical magnifier configured to visually magnify the outer skin layer of the patient as applicator device 410 is being coupled. Applicator device 410 can also be suitably coupled through a thin film of a low-loss coupling fluid, such as water or other commonly used coupling fluids for use with ultrasound transducers.

As discuss above, control system 402 can be configured in various manners for control of transducer 404. For example, control system 402 can comprise a processor, a display, and/or one or more input devices. Control system 402 can also comprise other devices and components, such power supplies, amplifiers, and/or filter devices. Such devices and components can be configured within a suitably electronic controls cabinet, housing or other enclosure. In accordance with an exemplary embodiment of the present invention, control system 402 comprises a drive circuit configured to control the operation of an exemplary ultra-high frequency ultrasound transducer.

An exemplary drive circuit can be configured in various manners. For example, with reference to FIG. 5A, a drive circuit 500 can comprise a driver 502 and a feedback network 504 configured in an oscillator-based, closed-loop arrangement to drive the frequency of transducer 404 in a controlled manner for maximum efficiency. In accordance with an exemplary embodiment, drive circuit 500 is configured to drive the frequency of the transduction element at the resonant frequency to facilitate maximum efficiency.

Driver 502 is configured to control power to a transduction element 506, e.g., a crystal or other suitable transduction element. Driver 502 can comprise various configurations. For example, driver 502 can comprise a power/oscillator driver, a linear power amplifier, or any other power source for providing power to drive a transduction element to create acoustical energy.

Feedback network 504 is configured to use electrical signals from driver circuit 502 and/or transduction element 506 to facilitate control of the frequency of operation, and thus provide optimum electro-acoustic conversion of energy. To maintain high electro-acoustical energy conversion efficiency, feedback network 504 can suitably facilitate control of the drive frequency to within a small fraction of the resonance frequency of transduction element 506.

Feedback network 504 comprises a closed-loop circuit, e.g., a self-oscillating or resonant circuit, to maintain the operating frequency of transduction element 506 in a manner that can enable optimum electro-acoustic conversion of energy. In other words, feedback network 504 is configured to cause driver circuit 502 to oscillate at the resonant frequency of frequency of transduction element 506, such as the frequency of crystal resonance. Feedback network 504 can create a 360-degree phase shift in the feedback loop of drive circuit 500. In addition, the configuration of feedback element 504 can provide a loop gain greater than or equal to one (1), thereby causing oscillation.

Figure 5A:
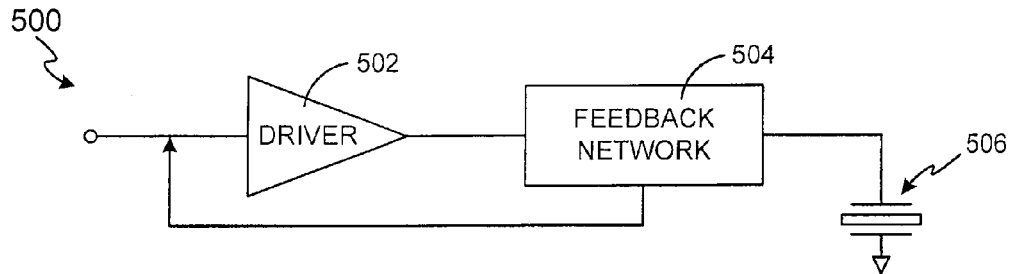
FIGS. 5A and 5B illustrate exemplary embodiments for control systems in accordance with the present invention.
Figure 5B:
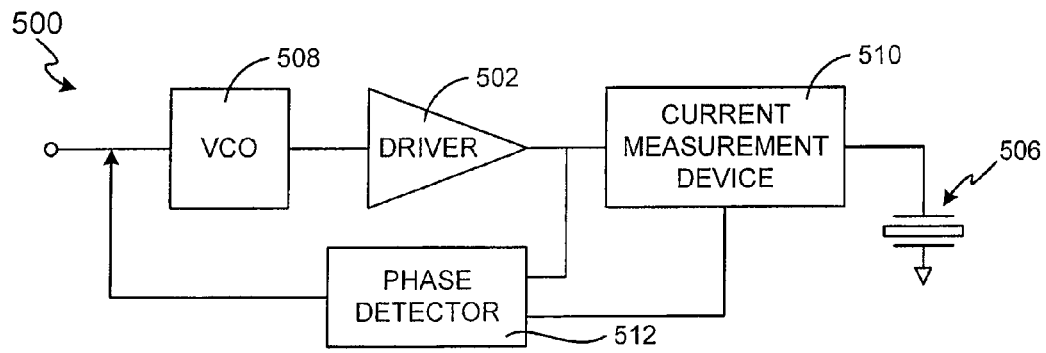

In addition to an oscillator-based drive circuit as illustrated in FIG. 5A, in accordance with another exemplary embodiment, with reference to FIG. 5B, drive circuit 500 can also comprise a voltage-controlled oscillator (VCO) based drive circuit. For example, drive circuit 500 can be configured with a power oscillator driver comprising driver 502 and a voltage-controlled oscillator (VCO) 508 and a feedback network comprising a current measurement device 510 and a phase detector 512. VCO 508 has an output signal coupled to the input of driver 502. VCO 508 can comprise any voltage-controlled oscillator circuit or device that can be configured to the nominal resonance frequency of the transduction element, e.g., the nominal resonance frequency of crystal 506. Current measurement device 510 can comprise one or more devices or components configured for measurement of the drive current from driver 502. For example, current measurement device 510 can comprise various current sensors, amplifiers or other measurement devices. Phase detector 512 is configured to receive voltage and current signals from driver 502 and current measurement device 510 and to provide a control signal to VCO 508. For example, since VCO 508 is configured to the resonance frequency of crystal 506, the current and voltage are in phase for crystal 506 since crystal tends to be resistive at the resonance frequency. However, when crystal 506 departs from the resonant frequency, the electrical impedance of crystal 506 becomes capacitive, and the current and voltage move out of phase. Thus, phase detector 512 can suitably measure the phases of the voltage and current and determine the phase differences to generate a correction voltage that can fine-tune the frequency of VCO 508 to the optimal frequency of oscillation.

Whether configured as an oscillator-based or VCO based drive circuit, or any other drive circuit configuration, drive circuit 500 can provide for high efficiency through electronic tuning, e.g., tracking of the optimal efficiency point, through use of a feedback network configured to facilitate control of the drive frequency to within a small fraction of the resonance frequency of transduction element 506. Since the resonant frequency of transduction elements can change due to loading, e.g., when application device 410 acoustically interfaces with the outer skin layers, drive circuit 500 can suitably control the drive frequency to thus maintain the optimum operating efficiency for a selected ultra-high frequency range of operation.

In addition, drive circuit 500 can be configured for driving transduction element 506 with either continuous waves of energy or short pulses of energy. Use of short pulses of energy can allow for an increase in the acoustic intensity level versus continuous waves of energy; however, drive circuit 500 is configured to make the acoustic intensity very large at the outer skin layers, e.g., the epidermis layer, and then have the acoustic intensity drop rapidly to lower levels, thus enabling continuous wave energy to also be used without detrimental effects to regions below the treatment regions of the patient. Moreover, by operating at optimum efficiency, the acoustic intensity can be suitably configured at high levels with use of moderate power output levels, e.g., a steady-state ultrasound intensity of approximately between 80 mW/cm$^2$ and 100 mW/cm$^2$ can cause sufficient but safe heating of the outer skin layer to facilitate treatment.

In accordance with another aspect of the present invention, an exemplary ultra-high-frequency ultrasound transducer system can be configured for providing ultrasound treatment to various regions within the superficial and/or internal superficial regions of the patient. For example, the region of treatment can be suitably moved below the superficial region through control of the frequency of the transduction element by suitably decreasing the frequency from ultra-high frequency levels, e.g., 300 MHz or more, to extremely high frequency levels, e.g., 100 MHz.

In addition, the region of treatment can also be suitably moved below the superficial region through the cooling of the exemplary application device for the transducer. For example, with reference again to FIG. 4B, through controlled cooling of applicator tip 414, conductive cooling can occur at the outer skin surface, e.g., proximate the point of contact of application device 410 and the outer skin layer. Accordingly, applicator tip 414 and the outer skin surface can come into thermal equilibrium, thus sparing the outer skin layer from heating effects that are effectively "pushed" below the superficial region. Such controlled cooling can be utilized with and without additional frequency control to move the treatment region below the superficial region.

In accordance with an exemplary embodiment, closed-loop temperature control can be suitably utilized to actively control the temperature of applicator tip 414. For example, the cooling can be achieved through circulating water through a water-circulating member configured proximate to or within application tip 414, such as a thin non-absorbing membrane that can retain water and allow circulation. In accordance with other exemplary embodiments, the application device 410 can be configured with electrical-based cooling control to suitably control the temperature of applicator tip 414, such as through the use of thermoelectric modules, heat sinks, and/or temperature sensors and the like configured proximate to or within application tip 414. As a result of controlled cooling of the temperature of application device 410 and/or the controlling of frequency, the region of treatment can be suitably moved below the superficial region.

In accordance with another aspect of the present invention, an exemplary ultra-high frequency transducer system may be configured to enable energy deposition at not only a fundamental frequency of transduction element 408 of transducer 404, but also at corresponding subharmonic frequencies of the piezoelectric or other acoustically-active material as well. Energy is provided to a treatment region at its peak when a piezoelectrically active material is driven at its fundamental frequency. Different piezoelectric and/or other acoustically-active materials have different fundamental frequencies. In accordance with an exemplary embodiment, energy can also be deposited at smaller peaks, i.e., at subharmonic frequencies, when the piezoelectric material is driven at its fundamental frequency. The use of the subharmonic characteristics of transducer 404 may be controlled and enabled through various focusing techniques.

Figure 6:
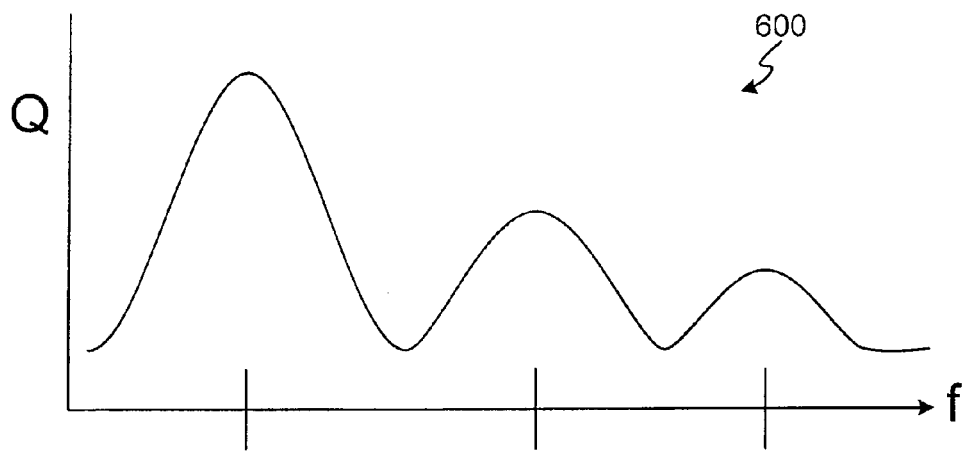
FIG. 6 illustrates an exemplary diagram of treatment characteristics of an exemplary transducer operating at the fundamental frequency and subharmonics in accordance with the present invention.

In accordance with an exemplary embodiment, enablement of the harmonics allows for treatment at various depths corresponding to the different harmonics. For example, with additional reference to frequency-harmonics curve illustrated in FIG. 6, ultra-high frequency transducer system 400 may treat various regions within the superficial and/or internal superficial regions of the patient, as represented by curve 600. Driving harmonic frequencies through transducer 404 enables treatment of a first superficial region, treatment of a second shallower region just below the former region, etc.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultra-high frequency ultrasound treatment with a transducer is described above is suitable for use by a medical practitioner proximate the patient, the control system can also be accessed remotely, i.e., the medical practitioner can view and/or operate the control system through a remote display or other remote I/O devices having imaging information transmitted in various manners of communication, such as by satellite/wireless or by wired connections such as IP or digital cable networks and the like, and can direct a local practitioner as to the suitably placement for the transducer. These and other changes or modifications are intended to be included within the scope of the present invention, as set forth in the following claims.

The invention claimed is:

1. A method for providing ultrasound treatment to a patient, the method comprising:
    operating a transducer to emit acoustical energy within a frequency range from about 10 MHz to about 30 MHz;
    coupling at least one acoustical matching layer of said transducer to an extracorporeal surface above a region of interest consisting of at least one of a superficial region and a subcutaneous region;
    focusing a first acoustical energy to a first depth in said region of interest;
    ablating a first portion of said region of interest;
    creating a first lesion in said region of interest;
    focusing a second acoustical energy to a second depth in said region of interest;
    maintaining said coupling at least one acoustic matching layer during and between said focusing said first energy and said focusing said second energy;
    ablating a second portion of said region of interest; and
    creating a second lesion in said region of interest.

2. The method according to claim 1, further comprising sparing tissue below said region of interest.

3. The method according to claim 1, further comprising imaging at least a portion of said region of interest.

4. The method according to claim 3, further comprising displaying said at least a portion of said region of interest.

5. The method according to claim 1, further sparing intervening tissue between said extracorporeal surface and at least one of said first lesion and said second lesion.

6. The method according to claim 1, further comprising:
    focusing a third acoustical energy to a third depth in said region of interest;
    ablating a third portion of said region of interest; and
    creating a third lesion in said region of interest.

7. The method according to claim 6, further comprising:
    maintaining said coupling at least one acoustic matching layer during and between said focusing said first energy, and said focusing said second energy, and said focusing said third energy.

* * * * *